United States Patent [19]
Trofast

[11] Patent Number: 5,980,949
[45] Date of Patent: *Nov. 9, 1999

[54] FORMULATION FOR INHALATION

[75] Inventor: Jan Trofast, Lund, Sweden

[73] Assignee: Astra Aktiebolag, Sweden

[*] Notice: This patent issued on a continued prosecution application filed under 37 CFR 1.53(d), and is subject to the twenty year patent term provisions of 35 U.S.C. 154(a)(2).

[21] Appl. No.: 09/005,100

[22] Filed: Jan. 9, 1998

Related U.S. Application Data

[63] Continuation-in-part of application No. 08/316,938, Oct. 3, 1994.

[30] Foreign Application Priority Data

Jan. 20, 1997 [SE] Sweden .................................. 9700136

[51] Int. Cl.⁶ .............................. A61K 9/14; A61K 9/16; A61K 9/72
[52] U.S. Cl. .............................................. 424/489; 424/45
[58] Field of Search ....................................... 424/45, 489

[56] References Cited

U.S. PATENT DOCUMENTS

| | | | |
|---|---|---|---|
| 4,199,578 | 4/1980 | Stevenson | 424/240 |
| 4,414,209 | 11/1983 | Cook et al. | 424/243 |
| 4,524,769 | 6/1985 | Wetterlin | 128/203.15 |
| 4,534,345 | 8/1985 | Wetterlin | 128/203.15 |
| 4,590,206 | 5/1986 | Forrester et al. | |
| 5,192,548 | 3/1993 | Velasquez et al. | 424/443 |
| 5,355,872 | 10/1994 | Riggs et al. | 128/200.21 |
| 5,474,759 | 12/1995 | Fassberg et al. | 424/45 |
| 5,503,869 | 4/1996 | Van Oort, I | 427/2.14 |
| 5,538,999 | 7/1996 | Clark et al., I | 514/65.3 |
| 5,551,489 | 9/1996 | Trofast et al. | |
| 5,562,923 | 10/1996 | Trofast et al., II | 424/489 |
| 5,614,514 | 3/1997 | Axelsson et al. | 514/174 |
| 5,628,307 | 5/1997 | Clark et al, II | 128/203 |
| 5,637,620 | 6/1997 | Trofast et al. | 564/630 |
| 5,647,347 | 7/1997 | Van Oort, II | 128/203 |
| 5,654,007 | 8/1997 | Johnson et al. | 424/489 |
| 5,655,523 | 8/1997 | Hodson et al. | 128/315 |
| 5,674,860 | 10/1997 | Carling et al. | 514/171 |
| 5,674,861 | 10/1997 | Andersson et al. | 514/174 |
| 5,700,410 | 12/1997 | Nakamichi et al. | 264/122 |
| 5,709,884 | 1/1998 | Trofast et al., II | 424/489 |
| 5,736,124 | 4/1998 | Akehurst et al. | 424/45 |

FOREIGN PATENT DOCUMENTS

| | | |
|---|---|---|
| WO 93/11773 | 6/1993 | WIPO . |
| WO 95/05805 | 3/1995 | WIPO . |
| WO 95/09616 | 4/1995 | WIPO . |
| WO 98/15280 | 4/1998 | WIPO . |

*Primary Examiner*—Shep K. Rose
*Attorney, Agent, or Firm*—Fish & Richardson P.C.

[57] ABSTRACT

A dry powder composition comprising terbutaline sulphate and a carrier substance, both of which are in finely divided form, wherein the formulation has a poured bulk density of from 0.28 to 0.38 g/ml is useful in the treatment of respiratory disorders.

10 Claims, No Drawings

FORMULATION FOR INHALATION

This is a continuation-in-part of U.S. application Ser. No. 08/316,938, filed Oct. 3, 1994 (pending).

FIELD OF THE INVENTION

The present invention provides a new pharmaceutical formulation, its preparation and its use.

BACKGROUND TO THE INVENTION

Potent drugs for administration by inhalation are generally formulated in association with carriers such as lactose because of the problem of preparing accurate doses. When such drugs are diluted, variations in the weight of the formulation result in a smaller drug dosage variation rate compared with when they are not diluted. These formulations have generally consisted of coarse particles of the carrier with fine particles of the drug, which combination is generally known as an ordered mixture.

The invention provides an improved formulation which, in systems designed to imitate inhalation has been found to give an improved dispersion of the drug.

DESCRIPTION OF THE INVENTION

According to the invention there is provided a dry powder composition comprising terbutaline sulphate and a carrier substance, both of which are in finely divided form, wherein the formulation has a poured bulk density of from 0.28 to 0.38 g/ml.

The poured bulk density according to the present invention is measured using known techniques, for example those described in "Powder testing guide: Methods of measuring the physical properties of Bulk powders" L. Svarovsky, Elsevier Applied Science 1987, pp 84–86.

The carrier substance is preferably a mono-, di- or polysaccharide, a sugar alcohol or another polyol. Suitable carriers are, for example, lactose, glucose, raffinose, melezitose, lactitol, maltitol, trehalose, sucrose, mannitol; and starch. Lactose is particularly preferred, especially in the form of its monohydrate.

The ingredients of the formulation according to the invention must both be in a finely divided form, i.e. their mass median diameter should generally be less than 10 $\mu$m, preferably from 1 to 7 $\mu$m, as measured by a laser diffraction instrument or a coulter counter. The ingredients may be produced in the desired particle size using methods known to those of skill in the art, e.g. milling, micronisation or direct precipitation.

The composition according to the invention is preferably formulated to comprise, as a daily dose, from 50 $\mu$g to 8 mg, more preferably from 100 $\mu$g to 4 mg and most preferably from 125 $\mu$g to 2 mg of terbutaline sulphate. More preferably the composition is formulated to provide unit doses of 125, 250 or 500 $\mu$g of terbutaline sulphate. The composition is preferably formulated to comprise in each unit dose from 50 $\mu$g to 25 mg of the carrier substance, more preferably from 50 $\mu$g to 10 mg, most preferably from 100 to 4000 $\mu$g.

According to the invention there is further provided a process for preparing a composition according to the invention which comprises (a) micronising terbutaline sulphate and the carrier substance;

(b) optionally conditioning the product; and (c) spheronizing until the desired bulk density is obtained.

The process preferably further comprises a low energy remicronisation step after step (b).

The formulation according to the invention may be made by conventional techniques known per se. Such production processes generally comprise micronising the ingredients to the required size, removing any amorphous areas on the particles obtained by, for example, the methods described in WO 92/18110 or WO 95/05805 and then agglomerating, spheronising and sieving the powder obtained. The size of the agglomerates obtained is preferably in the range of from 100 to 2000 $\mu$m, more preferably from 100 to 800 $\mu$m. The bulk density of the formulation produced may be adjusted by varying the components and the process empirically, for example the bulk density can be increased by lengthening the time in which the particles are tumbled in a spheronising device.

In solid-solid mixing, one of the most important features is to ensure content uniformity. The major problem encountered in the powder mixing of fine powders is the inability of mixers to break down powder agglomerates. It has been found that a remicronisation step after the conditioning step of the fine powder with low energy input is advantageous. It should generally be carried out using enough energy to break down powder agglomerates but not with so much energy that the size of the particles themselves is affected. Such a step gives a composition wherein the active substance and carrier substance are substantially uniformly distributed, having for example a relative standard deviation of less than 3% (preferably less than 1%) and does not disturb the crystallinity of the fine particles.

The formulation according to the invention may be administered using any known dry powder inhaler, for example the inhaler may be a single or a multi dose inhaler, and may be a breath actuated dry powder inhaler, for example Turbuhaler (trade mark). The invention further provides use of a composition according to the invention in the manufacture of a medicament for use in therapy. The composition according to the invention is useful in the treatment of respiratory disorders, particularly asthma. The invention also provides a method of treating a patient suffering from a respiratory disorder which comprises administering to the patient a therapeutically effective amount of a composition according to the invention.

The invention is illustrated, but not limited, by reference to the following Examples.

EXAMPLE 1

60 Parts of terbutaline sulphate were micronized to a mass medium diameter of less than 2 $\mu$m in a Alpin mill 100AFG and thereafter conditioned according to the method described in U.S. Pat. No. 5,562,923. 40 Parts of lactose monohydrate were micronized (Alpin mill 100AFG) down to a mass medium diameter of less than 3 $\mu$m and thereafter conditioned according to the method described in WO 95/05805. The micronized and conditioned terbutaline sulphate and lactose monohydrate were mixed thoroughly in a Turbula mixer. The mixture was remicronised in a spiral jet mill at a pressure of only about 1 bar to obtain an evenly distributed mixture. The powder was then agglomerated by feeding the powder into a twin screw feeder (K-Tron), sieving in an oscillating sieve (0.5 mm mesh size), spheronising in a rotating pan with a peripheral speed of 0.5 m/s for 4 minutes and then sieving again using the same sieve, then spheronising once more for 6 minutes before final sieving (mesh size 1.0 mm) giving a powder with a bulk density of 0.28 g/ml.

EXAMPLE 2

Example 1 was repeated with 30 parts of terbutaline sulphate and 70 parts of lactose monohydrate to give a powder with a bulk density of 0.31 g/ml.

I claim:

1. A dry powder pharmaceutical composition the active ingredient of which consists of terbutaline sulfate, the composition further comprising a carrier substance selected from the group consisting of monosaccharides, disaccharides, polysaccharides and polyols, wherein both the terbutaline sulfate and the carrier substance consist of particles having a mass median diameter of less than 10 μm, and wherein the composition has a poured bulk density of from 0.28 to 0.38 g/ml.

2. A composition according to claim 1 wherein the bulk density is from 0.30 to 0.36 g/ml.

3. A composition according to claim 1 wherein the active substance and carrier substance are substantially uniformly distributed.

4. A composition according to claim 1 for use in the treatment of a respiratory disorder.

5. A process for preparing a composition according to claim 1 which comprises (a) micronising terbutaline sulphate and the carrier substance;
(b) optionally conditioning the product; and
(c) spheronizing until the desired bulk density is obtained.

6. A process according to claim 5 which comprises a low energy remicronisation step after step (b).

7. A method of treating a patient suffering from a respiratory disorder which comprises administering to the patient a therapeutically effective amount of a composition according to claim 1.

8. A composition according to claim 1 wherein the carrier substance is selected from the group consisting of lactose, glucose, raffinose, melezitose, lactitol, maltitol, trehalose, sucrose, mannitol and starch.

9. A composition according to claim 8 wherein said carrier substance is lactose monohydrate.

10. A composition according to claim 1 wherein the mass median diameter is from 1 to 7 μm.

\* \* \* \* \*